(12) United States Patent
Morgantini et al.

(10) Patent No.: US 8,529,833 B2
(45) Date of Patent: Sep. 10, 2013

(54) METHOD AND APPARATUS FOR DISINFECTING ENCLOSED SPACES

(75) Inventors: Gianpiero Morgantini, Turin (IT); Maurizio Maletti, Nichelino (IT)

(73) Assignee: Officine Meccaniche Perjrani S.r.l., Turin (IT)

( * ) Notice: Subject to any disclaimer, the term of this patent is extended or adjusted under 35 U.S.C. 154(b) by 596 days.

(21) Appl. No.: 12/680,544

(22) PCT Filed: Feb. 21, 2008

(86) PCT No.: PCT/IB2008/050621
§ 371 (c)(1),
(2), (4) Date: Mar. 26, 2010

(87) PCT Pub. No.: WO2009/040684
PCT Pub. Date: Apr. 2, 2009

(65) Prior Publication Data
US 2010/0316530 A1    Dec. 16, 2010

(30) Foreign Application Priority Data
Sep. 28, 2007 (IT) .............................. TO2007A0683

(51) Int. Cl.
*A61L 2/22* (2006.01)
(52) U.S. Cl.
USPC ............. 422/29; 239/690; 239/700; 239/704
(58) Field of Classification Search
USPC ............................ 422/29; 239/690, 700, 704
See application file for complete search history.

(56) References Cited

U.S. PATENT DOCUMENTS

| | | | |
|---|---|---|---|
| 2,967,667 A * | 1/1961 | Norris | 239/701 |
| 4,540,124 A * | 9/1985 | Haruch | 239/223 |
| 4,564,375 A | 1/1986 | Munk et al. | |
| 4,723,726 A | 2/1988 | Ooishi et al. | |
| 4,887,770 A | 12/1989 | Wacker et al. | |
| 5,145,113 A | 9/1992 | Burwell et al. | |
| 5,433,387 A | 7/1995 | Howe et al. | |
| 5,474,236 A | 12/1995 | Davis et al. | |
| 5,947,377 A | 9/1999 | Hansinger et al. | |
| 6,003,784 A | 12/1999 | Van der Steur | |
| 6,053,437 A | 4/2000 | Hansinger et al. | |
| 6,056,215 A | 5/2000 | Hansinger et al. | |
| 6,189,813 B1 | 2/2001 | Skeath et al. | |
| 6,378,788 B1 | 4/2002 | Skeath et al. | |
| 6,513,736 B1 | 2/2003 | Skeath et al. | |
| 6,855,943 B2 | 2/2005 | Shields | |
| 2005/0139239 A1 | 6/2005 | Prae | |

FOREIGN PATENT DOCUMENTS

| | | |
|---|---|---|
| DE | 33 05 664 A1 | 8/1984 |
| EP | 0 394 629 A2 | 10/1990 |
| EP | 0 767 005 A1 | 4/1997 |
| EP | 0 857 515 A2 | 12/1997 |
| EP | 0 860 211 A1 | 8/1998 |
| FR | 2 481 782 | 11/1981 |

(Continued)

OTHER PUBLICATIONS

English language machine translation of JP 2005-308333, pub. Nov. 4, 2005, inventor: Asano et al.*

*Primary Examiner* — Sean E Conley
(74) *Attorney, Agent, or Firm* — Merchant & Gould P.C.

(57) ABSTRACT

A method and apparatus disinfects enclosed spaces by the dispersal of aerosols ionized alternately with negative and positive electrostatic polarity.

5 Claims, 2 Drawing Sheets

(56) References Cited

FOREIGN PATENT DOCUMENTS

| | | |
|---|---|---|
| FR | 2 758 476 A1 | 7/1998 |
| GB | 1 507 929 | 4/1978 |
| GB | 2 096 911 A | 10/1982 |
| JP | 2005/308333 | 11/2005 |
| SU | 1549540 A1 | 3/1990 |
| WO | WO 2005/025757 A2 | 3/2005 |

* cited by examiner

METHOD AND APPARATUS FOR DISINFECTING ENCLOSED SPACES

This application is a National Stage Application of PCT/IB2008/050621, filed 21 Feb. 2008, which claims benefit of Serial No. TO2007A000683, filed 28 Sep. 2007 in Italy and which applications are incorporated herein by reference. To the extent appropriate, a claim of priority is made to each of the above disclosed applications.

PURPOSE OF THE INVENTION

The present invention relates to a method and to apparatus for disinfecting enclosed spaces by aerosol means; the method and the apparatus have the characteristic that the aerosol is dispersed by negative and positive electrostatic charges alternately on the basis of the value reached by the intensity of the electrostatic field induced in the enclosed space under treatment; this has the result of reducing the dosages of disinfectant, of accelerating the treatment of disinfection of the air and of the surfaces, as well as of accelerating the precipitation of the particles in suspension as a result of induced growth in their size, thus achieving a quicker fall-out of the product after dispersal and use, with consequent greater productivity as a result of the shorter times that are required for safe access to the enclosed space after treatment.

DESCRIPTION OF THE RELEVANT PRIOR ART

The micro-organisms that are present in the air tend to remain in suspension as a result of the Brownian motion which is due to the fact that they repel one another. The repulsion results from the fact that the micro-organisms have similar structures to one another and because, as is well known, the electrical charges in the bipolar system of the cell membrane are of positive sign on the surface and of negative sign towards the protoplasm which is situated in the interior.

The efficacy of the disinfection of an enclosed space by aerosol means is affected by the size of the droplets since only those droplets which have dimensions of less than 5 μm, owing to the high value of the surface tension of the outer films of the droplets, constitute a dry aerosol which remains in suspension in the air with high mobility and which can interact with the micro-organisms suspended in the air.

On the other hand, the disinfection of an enclosed space also requires the treatment of surfaces which therefore need to be reached by droplets which are capable of wetting and which therefore have lower tension in the surface film and, in short, are of larger size.

Owing to their nature, conventional systems for producing aerosols for disinfection purposes produce a mixture of droplets of various sizes which fall within a range that varies according to the system but is generally from 1 to 20 μm, rendering it possible, in one way or another, to satisfy the two conflicting requirements.

However, whereas only droplets with sizes below 5 μm remain in suspension and can thus act on the micro-organisms, the larger droplets tend to fall rapidly within a short distance.

This leads to two problems. The first is that, with these conventional systems, the dosages of disinfectant have to be very high. Dosages up to more than 10 grams of disinfectant per cubic meter of enclosed space are generally required, according to the chemical/biological activity of the product used and to the type of apparatus.

In fact, with these conventional systems, in order to be able simultaneously to achieve contact both with the micro-organisms and with the surfaces, the mean of the Gaussian function of the droplet size must be around 10 μm in order to have both fine droplets which are in suspension and large, wetting droplets. Consequently, for each small droplet of between 1 and 5 μm which remains in suspension and which serves for the interaction with the micro-organisms in suspension, a roughly similar number of large droplets of between 15 and 20 μm are also produced; these fall rapidly, and for the most part remain unused in the vicinity of the generator.

To get an idea of the amount of product that may be lost, it should in fact be borne in mind that a falling droplet with a size of 20 μm has a weight 1,000 times that of a 2 μm droplet which remains in suspension. In short, with these conventional systems, a large amount of product is also wasted in view of the fact that long distribution periods are required to ensure that the necessary minimum quantity of small droplets is produced.

The second problem results from the fact that, with these systems, the hourly treatment capacity is generally low since long waiting times are required for safe access to the premises after treatment. The treatment cycles have an overall duration of between one and two hours, according to the volume of the premises. In fact, after dispersal, a pause of no less than 1 hour is required before entering, to avoid people inhaling the disinfectant which is still suspended on account of the fact that, even in still conditions and without taking Brownian motion into account, the precipitation time for particles with sizes of 1-5 μm is several hours, according to Stokes law.

With reference, by way of example, to the disinfection of fifty hotel rooms, with conventional methods using a single apparatus, almost 100 hours of work would be required. This is a prohibitive period of time, in view of the fact that the treatment can be performed solely during the short period in which, after the room has been left empty, it remains at the disposal of service personnel in order to be put in order. If 2 hours are available for putting the rooms in order, as many as fifty sets of apparatus will be required, that is one per room, whereas only four sets of apparatus would suffice if the treatment had an overall duration of only 10 minutes.

Basically, it is clear that the effective capacity of an apparatus for disinfecting enclosed spaces is directly proportional to the content of ultra-fine droplets present in the aerosol that is dispersed, and inversely proportional to the waiting time that is required for the fall-out of the disinfectant after its dispersal.

At the moment, aerosols for disinfecting enclosed spaces are produced mainly by Venturi nozzles. Systems with rotary atomizers are not used in practice for disinfecting enclosed spaces but are used more widely in agriculture and for painting.

There is also a system which uses the piezo-electric effect. It is generally used solely for air humidification since piezo-electric transducers are unsuitable for operation with solutions of chemical products, particularly of corrosive products such as, for example, hydrogen peroxide and peracids. Moreover, there is a screen system which, although it is quite widespread, has great limitations, as will be discussed further below.

In any case, in none of the patent literature relating to various atomization and nebulization systems are there applications similar to the present one in which the size of the particles in suspension after dispersal is controlled by ionization and with alternating sequences of electrostatic fields of opposite polarities.

In nebulization by the Venturi effect, the liquid is divided into small droplets by means of compressed air which is caused to pass, together with the liquid, through nozzles containing converging/diverging orifices. A mist in which the droplets have quite varied sizes, at best between 1 and 20 µm with a Gaussian mean of about 10 µm, is obtained.

This size distribution results from the fact that the nebulization takes place by a process which is linked to the turbulence of the fluid threads, that is, which is essentially random. Moreover, in the regions in which the concentration of droplets being formed is high, some of the droplets just formed coalesce and join together forming further, larger droplets both because of the high probability of meetings and because of the electrostatic charges of opposite sign which the droplets and the materials acquire owing to the breaking-up of the liquid and to friction. With this method, the size distribution is therefore broad and the percentage of droplets with sizes of about 1 µm is small.

In fact, in order to reduce the droplet size, sound or ultrasound resonators are added downstream of the Venturi in some applications. This is the case in the following patents: FR 2 481 782 filed by Wanson, FR 2 758 476 by Klein, EP 0 394 629 by Caldyn Apparatebau, DE 33 05 664 by Kurosaki Refractories, GB 1 507 929 by Mitsubishi Precision, GB 2 096 911 by Simpkins, U.S. Pat. No. 4,564,375 by Munk, U.S. Pat. No. 6,513,736 by Corning Inc., EP 1 682 279 by Gloster Santé Europe.

With reference, in particular, to the teachings of EP 1 682 279 which was filed in 2003 and is intended expressly for the dispersal of aerosols which are as fine as possible for the disinfection of enclosed spaces, it is pointed out that the distribution of droplets obtained is also quite broad in this case since it is stated to be "of the order of from 2 to 20 µm diameter with a Gaussian mean between 7 and 15 µm".

The nebulization system that is based on the rotary atomizer, that is, that which is used in the present invention, is constituted basically by a cup or bell which is kept in rotation at a high speed, generally within the range of between 15,000 and 60,000 revolutions per minute. The material, which is generally introduced in the centre, is thrown out by the bell by centrifugal force, and the stream of droplets is then deflected in the desired direction by a compressed-air jet or by a fan. This method produces droplets with a narrow size distribution and is used particularly in painting systems, especially in electrostatic painting systems, and in the agricultural field. In these applications, particularly fine droplets are not required, the optimal droplet size being around 30 µm, but a narrow size distribution, which the system can achieve, is required.

In electrostatic painting applications, a direct-current electrical voltage of the order of between 40 and 100 kV is used to charge the droplets electrically so that they are attracted by the part to be painted which is placed in front and connected to the other terminal of the voltage generator. In all of these systems, the electric charge is imparted to the aerosol with a fixed and constant polarity (either positive or negative) at the moment at which the product comes into contact with the rotary bell to which a voltage is applied in various ways. These systems are described in particular in EP 0 857 515 A3 by Illinois Tool Work Inc., U.S. Pat. No. 4,723,726 by Toyota et al., U.S. Pat. No. 4,887,770 by Wacker et al., U.S. Pat. No. 5,474,236, U.S. Pat. No. 5,433,387 by Ransburg Corp., U.S. Pat. No. 5,947,377 and U.S. Pat. No. 6,053,437 by Nordson Corp., U.S. Pat. No. 6,003,784 by Gunnar Van de Steur.

Another nebulization method uses piezoelectric devices which, by oscillating at high frequency, bring about oscillation of the liquid which is placed in contact; the liquid breaks up into particles that are then drawn along by an air-flow. These systems are described in EP 0 860 211 filed by Degussa, U.S. Pat. No. 5,145,113 by United Technologies Inc., and U.S. Pat. No. 6,855,943 by Northrop Grumman Corporation. Finally, there is another system which uses the Rayleigh break-up effect and which is described in U.S. Pat. No. 6,189,813 and U.S. Pat. No. 6,378,788 filed by Corning Inc.

In screen systems, the liquid is sprayed against a mesh by means of a bladed rotor which draws the liquid from a tank, bringing about the formation of droplets of greatly varying sizes upon impact. Naturally, electrostatic charges of mixed sign are also produced upon impact, owing to friction. Only the finest droplets are drawn away as an aerosol by an air-flow. The larger droplets, on the other hand, fall into the tank, as do those which are formed in the meantime from the fine droplets owing to static electricity and coalescence phenomena.

This apparatus, which is used in the domestic field for the most part simply as humidifiers, produce an aerosol with minimum droplet sizes of about 15-20 µm because, if the speed of the air-flow is reduced so as to draw along only smaller droplets, production becomes negligible. The relatively large droplet size enables disinfection to be achieved solely in the vicinity of the apparatus and regions which are in shadow relative to the mist generator are treated with difficulty, resulting in high dosages and great wastage of product.

None of the applications or methods indicated above or others that are based in some way thereon claim any control of the growth of the droplets and of the particles in suspension after dispersal, or of their fall-out, by means of alternating cycles with reversed polarity of the electrostatic field or by other methods.

Except for the disinfection of enclosed spaces, in most applications, there would be no point in firstly producing fine droplets and then causing them to grow in size after they had been dispersed in the air. In painting, the size of the droplets emitted by the nebulization system should be no less than 25 µm to prevent the product from drying too soon which would lead to the production of regions with a coarse and rough finish. In agricultural spraying, it is also necessary to prevent the nebulization system from producing excessively small droplets so as to prevent dispersal onto other land and loss of product.

DESCRIPTION OF THE INVENTION

Figure 4:
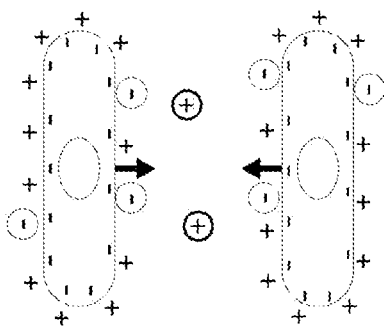
FIG. 4 is a diagrammatic view of the micro-organisms and their polarities of FIG. 3 attracting micelles.

The method and the apparatus for disinfecting enclosed spaces of the present invention use a rotary atomizer as the aerosol generator in combination with further components which are essential for achieving the results indicated. These results consist, in comparison with conventional systems, of a considerable reduction in the dosage of disinfectant, of the acceleration of the disinfection treatment both of air and of surfaces, and of the achievement of a quicker fall-out of the product after dispersal, resulting in greater productivity and shorter times required for safe access to the enclosed space after treatment.

The rotary atomizer used is constituted by a bell which is rotated at high speed. The rotation divides the liquid supplied into small droplets which leave the outer edge by centrifugal force.

In the present application, suitable measures are used to prevent the small droplets, once formed, from combining in uncontrolled manner to form larger droplets by coalescence or attraction. By generating an electrostatic field in the aerosol formation region, the same polarity of electric charge is applied to the individual droplets emitted. Moreover, the electrostatic field is dispersed with the same polarity into the enclosed space under treatment. Since the droplets have the same electrostatic polarity from the moment at which they are formed, they tend to repel one another so that they continue on their path until they are attracted by particles of opposite polarity that are already present or have previously been dispersed in the enclosed space.

The intensity and polarity of the electrostatic field in the enclosed space under treatment is preferably measured constantly by an instrument inside the aerosol generator. On the basis of the measurement, the programmable control system of the apparatus reverses the polarity of the electrostatic field when it reaches the predetermined level of saturation in the enclosed space under treatment. Less preferably, the polarity may also be reversed at programmed times and on the basis of experimental observations and measurements.

These measures control the aggregation of the particles which takes place exclusively towards particles with charges of opposite sign, after dispersal into the enclosed space and when decided by the controller of the process. Moreover, the droplets are thrust from the apparatus towards the enclosed space without the use of compressed air or any system which leads to compression, preventing concentration of the droplets and the generation of uncontrolled electrostatic charges.

The aerosol dispersed by the apparatus is dry with ultra-fine droplets with a narrow distribution, preferably within the range of between 1 and 5 μm and with a Gaussian mean of about 2.5 μm. The fineness of the droplets enables the disinfectant to be dispersed to every part of the enclosed space by Brownian motion, thus achieving the disinfection treatment even in regions and on surfaces which are not directly exposed.

The rotary atomizer is a device which is used in drying, in painting, and in agriculture. In the painting field, it is used, as an alternative to the Venturi nebulization system, because it produces a mist with droplets of precise size with a minimal size distribution. In painting, the system is often combined with electrostatic systems which direct the polarized mist onto the object to be painted which is kept polarized with the opposite sign. A direct-current electrical voltage of the order of between 40 and 100 kV is used to charge the droplets electrically so that they are attracted by the part to be painted which is placed in front and connected to the other terminal of the voltage generator.

In all of these systems, the electric charge is imparted with a fixed and constant polarity (either positive or negative) at the moment at which the product comes into contact with the rotary bell, to which a voltage is applied in various ways. The system is regulated so as to prevent the production of excessively small droplets, to reduce loss of paint, and to improve the quality of the finished product. In general, it is sought to obtain an optimal droplet size of about 25 μm and a jet with the maximum possible concentration of droplets.

In use for painting, the rotary bell is thus deliberately surrounded by a compressed-air jet which has the purpose of compressing and directing the jet, keeping the concentration of droplets high along the entire path from the atomizer to the object to be painted.

In the spraying of products for agriculture, on the other hand, the mist must also be constituted by droplets no smaller than 25 μm in order for the mist to be sufficiently heavy as soon as it is formed and to be able to wet the crop readily, preventing losses of product and dispersal outside the area under to treatment because of wind.

In contrast, the method and the apparatus of the present invention are intended for the production of an aerosol jet with droplets that are as small as possible and with the least possible concentration per unit of volume, that is, with maximum dilution in the transporting aeriform flow. By means of electrostatic fields and controlled reversal of the polarization, starting with purely fine droplets, this system can firstly cause the fine droplets to interact with the micro-organisms and then enlarge the droplets that are already dispersed in the air to a size suitable for wetting surfaces, thus using a minimal quantity of disinfectant.

As already stated, the efficacy of the disinfection of an enclosed space by aerosol means is affected by the size of the droplets; only droplets having dimensions below 5 μm remain in suspension in the air forming a dry aerosol which can move by Brownian motion with the ability to interact with the micro-organisms suspended in the air. On the other hand, the disinfection of an enclosed space also requires the treatment of the surfaces which must be reached by larger droplets that are capable of wetting.

The fact that, with the innovative system described herein, the aerosol is produced with purely ultra-fine droplets which are caused to grow in size only subsequently brings the advantage that decidedly smaller dosages, down to less than one tenth, are required in comparison with conventional disinfection systems. The aerosol is generated so as to produce, by means of the rotary atomizer, purely droplets up to sizes of between 1 and 5 μm with a Gaussian mean of about 2.5 μm so that all of the product dispersed remains in suspension in the air during the first stage of the operation.

Another feature is that, at the moment when the aerosol is emitted into the enclosed space under treatment, it is supplied with electrostatic charges by the alternation of periods of negative polarity and periods of positive polarity. This brings various advantages. The first is that, since the droplets just formed are electrically polarized with the same sign, they tend to repel one another, preventing uncontrolled growth by aggregation and coalescence.

Figure 1:
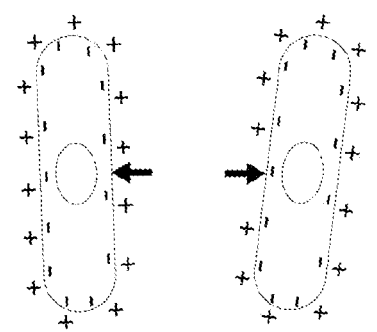
FIG. 1 is a diagrammatic view of micro-organisms and their polarities in air.

The second advantage is the ability to interact rapidly with the micro-organisms in suspension in the air. As is known, in the bipolar system of the cell membranes of micro-organisms, the electric charges are of positive sign on the surface and of negative sign towards the protoplasm which is in the interior. Consequently, since the micro-organisms have the same positive charge on the surface, they tend to repel one another (FIG. 1).

Figure 3:
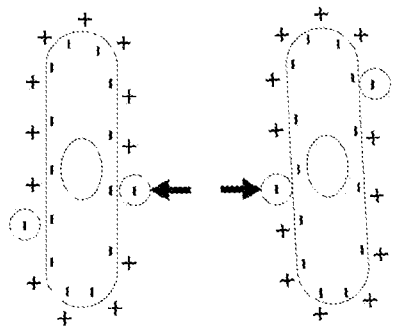
FIG. 3 is a diagrammatic view of micro-organisms and their polarities in an aerosol with negative ions.
Figure 2:
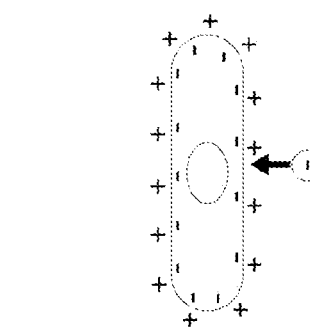
FIG. 2 is a diagrammatic view of a micro-organism and its polarities in an aerosol.

If an aerosol of fine, negatively charged droplets is dispensed initially, these are attracted by the outer membranes of the micro-organisms (FIG. 2). This procedure is not novel and there are various air purifiers on the market which emit negative ions. However, it should be pointed out that, since the particles that are produced simply by aggregation between particles in suspension in the air and negative ions are not electrically neutral but have a free negative electric charge, they repel one another with even greater force than that of the original micro-organisms (FIG. 3). If disinfectant is dispersed in this way, it comes into contact with the particles in suspension but the new particles formed by aggregation still remain in suspension both because they repel one another electrically and because their size remains very small.

The method and the apparatus of the present invention are not limited to the dispersal of negative ions but stages in which aerosols with negative electric charge are dispersed alternate with stages in which aerosols with positive charge are dispersed. The process starts with a stage in which aerosols with negative charge are dispersed. When the electrostatic-field meter with which the apparatus is provided detects that the air in the enclosed space has reached the predetermined field level, the polarity is reversed, so that aerosols with positive charge are dispersed.

Figure 7:
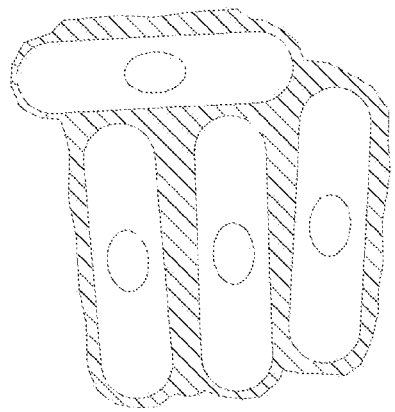
FIG. 7 is a diagrammatic view of grown heavy aggregates.
Figure 6:
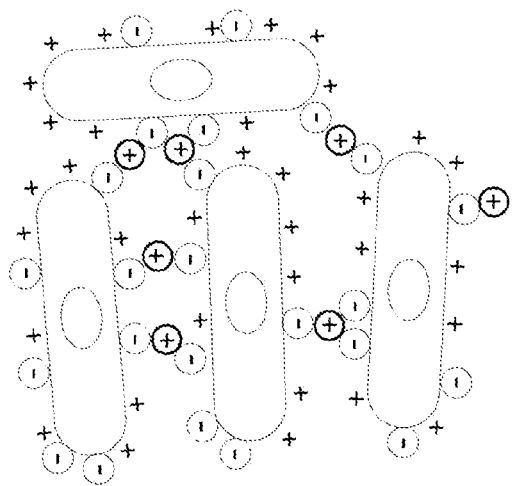
FIG. 6 is a diagrammatic view of grown aggregates and their polarities.
Figure 5:
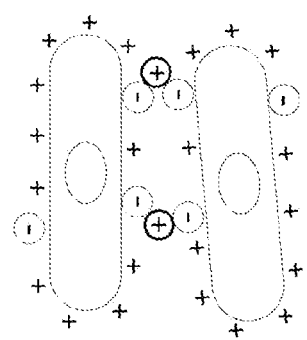
FIG. 5 is a diagrammatic view of new aggregates and their polarities.

By electrical attraction, the positive droplets that are now dispersed attract the previously formed, aggregated micelles, which have negative charge (FIG. 4). New aggregates are created (FIG. 5) which then grow further (FIG. 6) thus coating the micro-organism and making it considerably heavier (FIG. 7).

The dosage of disinfectant, which depends on the volume of the premises to be treated, is thus divided into several stages which are performed in sequence with a change in the polarity of the electrostatic charge transported each time. In the minimal configuration of the process, a cycle is performed that is composed of two dispersal stages, the first with negative polarity and the second with positive polarity. The cycle composed of a dispersal with negative charge followed by a dispersal with positive charge may be performed one or more times, preferably several times, in order to bring about greater growth of the particles in suspension until they are caused to fall out.

Figure 8:
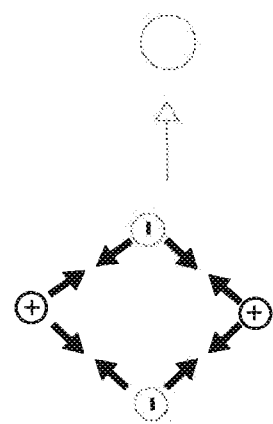
FIG. 8 is a diagrammatic view of droplets for wetting surfaces.

The dispersal of aerosols with opposite electrical charges in sequence also means that the droplets which have not had an opportunity to combine with micro-organisms will join with others of opposite sign by electrical attraction, thus bringing about the formation of the larger droplets which are required to wet the surfaces (FIG. 8) and at the same time eliminating the suspended fine droplets by fall-out when they are no longer required.

The alternation of electric charge in the aerosol thus achieves firstly the dispersal of droplets which can come into contact with the micro-organisms and then the formation of larger particles which fall as fall-out with neutral electric charge. These new particles easily wet the surfaces and are separated from the air into which they were admitted as fine droplets within a very short period of time of the order of a few minutes, in comparison with hours in conventional disinfection systems. This also applies to the aerosol droplets which are not bound in any way to the micro-organisms in suspension.

In the apparatus of the present invention, particular care is taken with the shape and details of the bell and of the transportation and dispersal system so that only very fine droplets are formed. Instead of directing the jet by means of compressed air as in most conventional applications, which would involve a region of compression of the aerosol and consequently concentration and coalescence of the droplets into other, larger droplets, the jet is controlled gradually by means of two concentric laminar flows of transporting air which is blown progressively so that there are never regions in which the aerosol is subjected to compression.

The laminar flow which first encounters the jet has the purpose of permitting a first broadening of the aerosol jet. The second laminar flow has the task of further diluting the jet and thrusting it as far as possible, as well as supplying the electrostatic charges. These are produced by a suitable corona-discharge device arranged in a manner such that it can reverse the polarity of the field and of the ions emitted when the intensity of the electrostatic field of the air in the enclosed space under treatment has reached a predetermined value preset in the program of the apparatus, or on the basis of time and test data.

Figure 10:
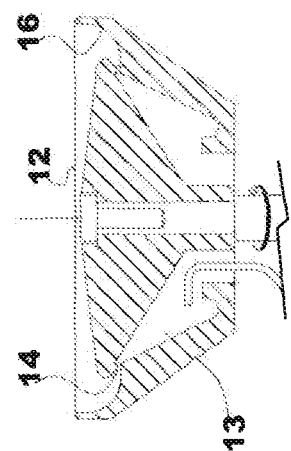
FIG. 10 is a diagrammatic sectional view of a bell for the apparatus shown in FIG. 9.
Figure 9:
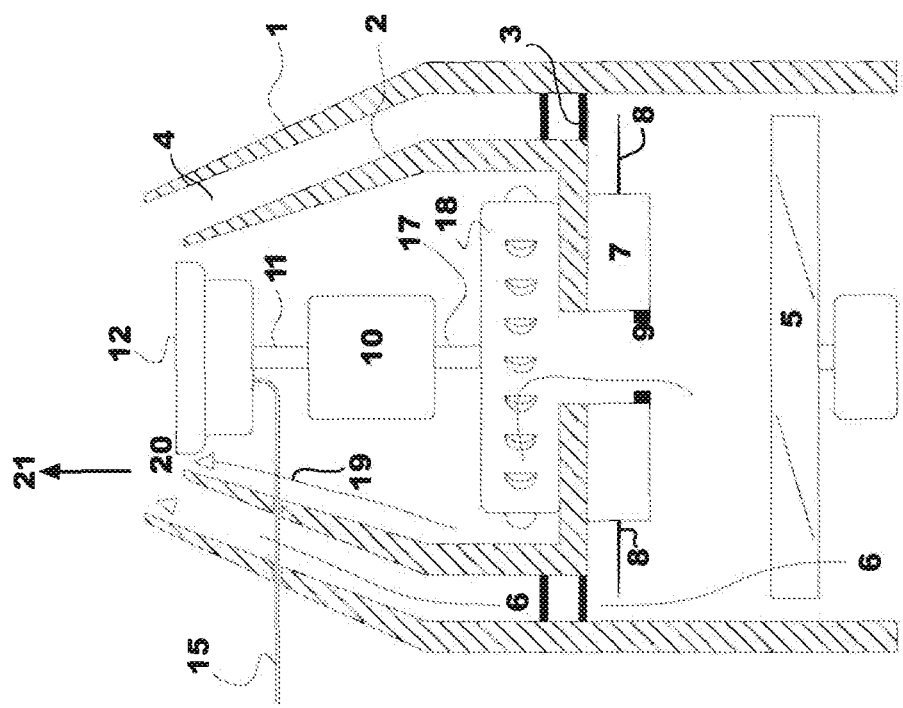
FIG. 9 is a diagrammatic view of an apparatus for aerosol production.

With reference to FIGS. 9 and 10, the liquid to be micronized is introduced into the central chamber 13 of a bell 12 which communicates with the exterior through a series of small holes 14 which are arranged in a radial or inclined manner. The bell rotates at a speed of between 10,000 and 100,000 revolutions/minute, preferably 30,000 revolutions/minute, producing a film of liquid which is cut by the inner edges of the rapidly rotating holes, bringing about the formation of droplets of a regular size of between 1 and 5 µm which leave the bell by centrifugal force. The droplets are collected by a primary laminar air-flow so that a finely-dispersed aerosol is created.

The aerosol flow is immediately mixed with a secondary air-flow which has previously been charged with static electricity by means of an electrostatic-field generator which operates on the basis of corona discharge and at the dispersive power of the electrode tips. The flow is generated by a fan with a high output so as to provide for the maximum dilution and for a flow with a thrust adequate for the treatment of enclosed spaces even of considerable volume and dimensions.

The electrostatic charge of the aerosol is produced in the apparatus by an electric field generated by electrode tips to which a voltage of between 2,000 and 20,000 V, preferably less than 10,000 V to prevent the production of ozone, is applied. The field generator is constructed so as to be able to reverse the sign of the polarity. Moreover, it has a sensor which measures the intensity of the electrostatic field present in the enclosed space under treatment by measuring it in the air entering the apparatus. This measurement system is used by the control system of the apparatus to establish the optimal moment for the reversal of the electrostatic charge imparted to the aerosol. Alternatively, although less preferably, the polarity of the electrostatic field may also be reversed after predetermined and programmed periods of time.

In the first dispersal stage, the electrostatic charge imparted to the aerosol is always of negative polarity so that the droplets can combine, by attraction, with the micro-organisms which have positive surface charge.

The dry aerosol is detached from the apparatus by a flow which is preferably directed upwards although any angle of dispersal may be used because the small size of the aerosol droplets allow the aerosol to be dispersed at great speed in any direction, even reaching the regions that are in shadow relative to the apparatus.

The apparatus of the invention is defined by the appended claims. In particular, the apparatus comprises:
  an outer casing of non-conductive material, preferably of combined cylindrical and conical shape with a vertical axis,
  an inner casing of non-conductive material, preferably of combined cylindrical and frustoconical shape with a vertical axis, which is arranged so as to form a chamber for the passage of air between the two casings,
  a high-speed rotary bell arranged inside the inner casing and in the vicinity of one end thereof and formed with a diameter such that an annular passageway remains clear between the bell and the output edge of the inner casing, an air blower acting in a manner such that the air is forced to pass in laminar form through the above-mentioned annular passageway, a shape of the rotary atomizer bell such as to form an inner annular chamber into which the liquid is dosed and which communicates, by means of small holes, with the exterior which has a concave shape so as to facilitate the deflection of the droplets, a fan for generating an air-flow in the chamber existing between the outer casing and the inner casing, means suitable for creating an electrostatic field and for rendering the aerosol output by the apparatus ionized alternately with negative polarity and with positive polarity, optionally, means which can measure the electrostatic charge in the enclosed space under treatment, means suitable for dosing the liquid that is to form the aerosol into a chamber disposed inside the rotary atomizer bell, a programmable system for dosing the aerosol in dependence on the volume of the enclosed space to be treated, on the dosages required, and on the type of disinfectant, as well as for performing the various stages of the cycle, including the monitoring and reversal of the electrostatic charge of the aerosol, which is preferably produced on the basis of the measurement of the electrostatic charge present in the enclosed space under treatment.

Further advantages and characteristics of the method and of the apparatus according to the invention will become clear from the following detailed description relating to appended FIGS. 9 and 10, which are provided purely by way of non-limiting example and which show schematically an apparatus for implementing the aerosol-production method.

The apparatus is defined by an outer casing 1 of non-conductive material and preferably of combined cylindrical and frustoconical shape with a vertical axis. An inner casing 2 of non-conductive material and preferably of combined cylindrical and frustoconical shape with a vertical axis is positioned inside the outer casing 1 and is held in position by means of spacers 3 so that a clear passageway 4 remains between the two containers.

A fan 5, which produces an air-flow 6, is arranged in the lower part of the casing 1. An electrostatic field generator 7 is arranged above the fan 5 and has electrode tips 8 and a system 9 for measuring the intensity of the field in the entering air. The device operates at a voltage of between 2,000 and 20,000 V, preferably below 10,000 V to prevent the production of ozone. The field generator is constructed so as to be able to reverse the polarity of the field and of the ions emitted. The measurement system 9 comprises a capacitive or equivalent sensor which, together with suitable electronic systems, can determine the intensity of the electrostatic field present in the enclosed space under treatment by measuring it in the air entering the apparatus. This measurement system is used by the control system of the apparatus to establish the optimal moment for the reversal of the electrostatic charge imparted to the aerosol.

A motor 10 is installed inside the inner casing 2 and drives the rotary bell 12 of the atomizer by means of a shaft 11. The bell 12 has an inner chamber 13 which conveys the liquid by centrifugal force towards holes 14 which are formed radially at right angles or at an inclination so as to cut the liquid film which is formed in the inner chamber 13 after being admitted through a duct 15.

The bell is rotated at a speed of between 10,000 and 100,000 revolutions/minute, preferably 30,000 revolutions/minute. During rotation, the holes cut the liquid film into extremely fine droplets which are thrown out into the concave portion 16 of the bell.

The motor 10 also drives, by means of a shaft 17, a blower 18 which produces an air-flow 19 that is discharged into a passageway 20. Alternatively, the air-flow 19 may also be produced by means of a separate blower and, likewise, the blower 18 may be driven by a motor separate from the motor 10.

The combination of the air-flows 6 and 19 with the droplets thrown out from the rotary bell 12 forms the aerosol 21 polarized with electrostatic charge.

The apparatus is completed by devices for rotating the motor 10 at the speed set, systems for monitoring the electric field in the air of the enclosed space under treatment and for reversing the polarity of the electrostatic field generated, and devices for programming the treatment in dependence on the volume to be treated, on the dosage, and on the type of disinfectant.

The invention claimed is:

1. A method of disinfecting an enclosed space comprising emission of liquid disinfectant in aerosol form having ultra-fine droplets, wherein said aerosol is produced by a rotary atomizer adapted to generate droplets with a maximum size no greater than 5 μm; charging the aerosol in alternate stages, with negative electrostatic charge or with positive electrostatic charge by an electric field; the electric field have a polarity which is reversed based on measurement of intensity of an electrostatic field present in the enclosed space being treated.

2. A method according to claim 1 in which the polarity of the electrostatic field is reversed on the basis of the measurement of the intensity of the electrostatic field present in the enclosed space under treatment, or after predetermined and programmed periods of time.

3. A method according to claim 1, wherein time of the reversal of the polarity of the electrostatic field is selected to cause controlled growth of the size of the particles that are already present or are admitted in suspension in the air.

4. A method according to claim 3, wherein the controlled growth of the particle size causes a dimensional increase of the droplets of disinfectant admitted to the enclosed space, which grow from the initial size of less than 5 μm to a larger size capable of wetting surfaces.

5. A method according to claim 3, wherein the controlled growth of the particles causes fall-out of the particles with consequent rapid elimination of the micronized disinfectant previously admitted to the enclosed space, after use.

* * * * *